(12) United States Patent
Magagnoli et al.

(10) Patent No.: US 11,304,809 B2
(45) Date of Patent: Apr. 19, 2022

(54) TEMPORARY SPACER DEVICE FOR JOINTS OF THE HUMAN BODY

(71) Applicant: Cossington Limited, Kingston upon Thames (GB)

(72) Inventors: Augusto Magagnoli, Cervia (IT); Robert Michael Meneghini, McCordsville, IN (US); Bryan Donald Springer, Charlotte, NC (US); Scott Matthew Sporer, Wheaton, IL (US); Stephen Joseph Incavo, Houston, TX (US)

( * ) Notice: Subject to any disclaimer, the term of this patent is extended or adjusted under 35 U.S.C. 154(b) by 0 days.

(21) Appl. No.: 15/733,548

(22) PCT Filed: Mar. 7, 2018

(86) PCT No.: PCT/IB2018/051481
§ 371 (c)(1),
(2) Date: Aug. 25, 2020

(87) PCT Pub. No.: WO2019/171139
PCT Pub. Date: Sep. 12, 2019

(65) Prior Publication Data
US 2020/0397587 A1    Dec. 24, 2020

(51) Int. Cl.
*A61F 2/30* (2006.01)
*A61F 2/38* (2006.01)

(52) U.S. Cl.
CPC ........... *A61F 2/30724* (2013.01); *A61F 2/38* (2013.01); *A61F 2/389* (2013.01); *A61F 2/3859* (2013.01); *A61F 2/30771* (2013.01); *A61F 2002/30332* (2013.01); *A61F 2002/30359* (2013.01); *A61F 2002/30518* (2013.01); *A61F 2002/30672* (2013.01); *A61F 2002/30677* (2013.01)

(58) Field of Classification Search
CPC ........... A61F 2/38; A61F 2/389; A61F 2/3868
See application file for complete search history.

(56) References Cited

U.S. PATENT DOCUMENTS

| 5,133,760 A | 7/1992 | Petersen |
| 2006/0030945 A1* | 2/2006 | Wright ............... A61F 2/30734 623/20.15 |
| 2015/0134068 A1 | 5/2015 | Leonard |

FOREIGN PATENT DOCUMENTS

| EP | 1623686 | 2/2006 |
| EP | 1900345 | 3/2008 |
| WO | 03065939 | 8/2003 |
| WO | 2016063156 | 4/2016 |

* cited by examiner

*Primary Examiner* — Jason-Dennis N Stewart
(74) *Attorney, Agent, or Firm* — Themis Law

(57) ABSTRACT

A temporary spacer device for a joint of the human body such as a knee joint includes a first component or femoral component, adapted to be constrained to a bone or to the femoral bone of a patient, at the joint of the human body; a second component or tibial component, adapted to be constrained to a bone or tibial bone of a patient, at the joint of the human body, and at least one stem having a proximal end, wherein the first component or femoral component and/or the second component or tibial component include at least one housing seat for the proximal end of the at least one stem, adapted to allow the inclination and/or rotation of the at least a stem with respect to an insertion axis of the proximal end into the at least one housing seat.

20 Claims, 3 Drawing Sheets

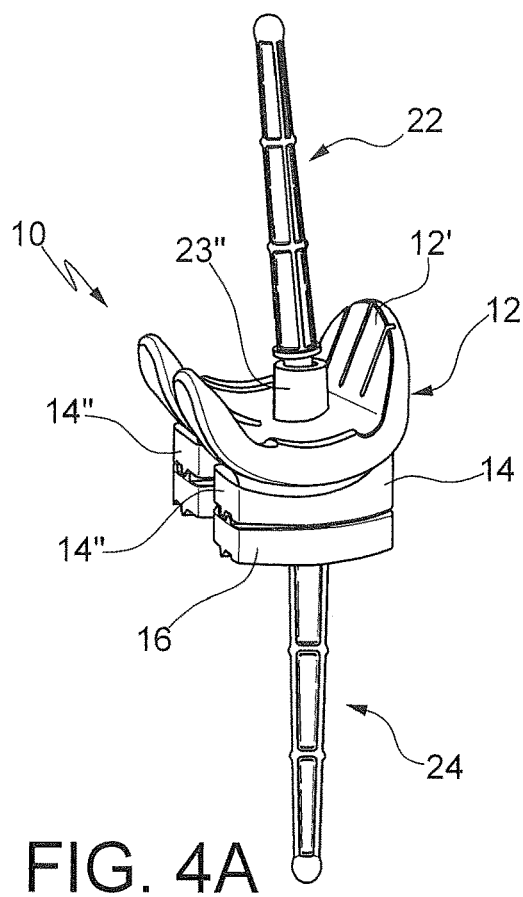
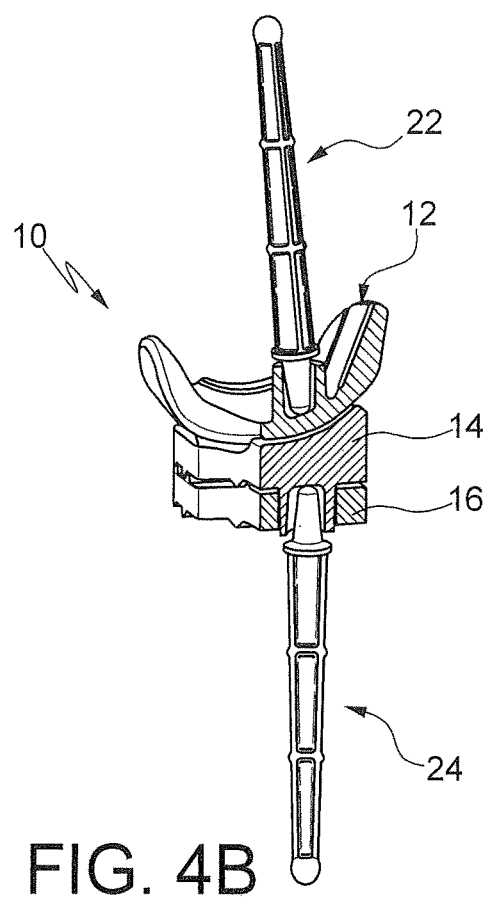
FIG. 4A    FIG. 4B
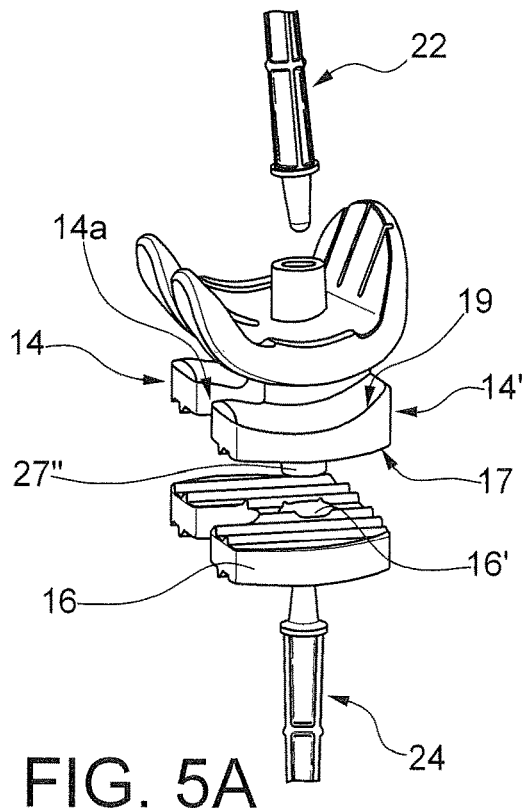
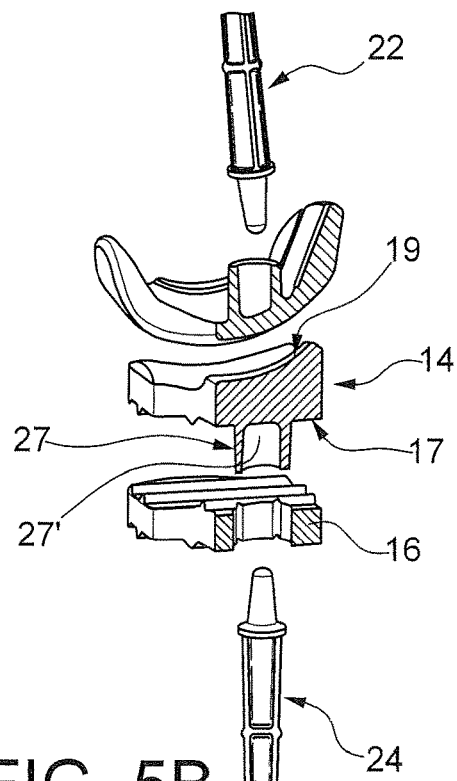
FIG. 5A    FIG. 5B

TEMPORARY SPACER DEVICE FOR JOINTS OF THE HUMAN BODY

TECHNICAL FIELD OF THE INVENTION

The present invention relates to a spacer device able to replace, for at least a certain period of time or temporarily, an infected articular prosthesis.

More particularly, the present invention relates to a spacer device provided with a stem.

PRIOR ART

It is known that, in an articular prosthesis present in an anatomical site of the human body, such as a joint, infections or damages may arise such that it is necessary to remove the prosthesis itself.

In the moment in which a prosthesis is removed, it is now common practice to insert—in its place—a joint spacer device that is of a temporary nature, as it remains in the implantation site the time between the removal of the infected or damaged prosthesis and the implantation of a second prosthesis.

This spacer device can comprise one or more pharmaceutical or medical substances, such as for example one or more antibiotics, in order to treat the current infection at the site where the removed prosthesis was previously inserted.

During this period, the spacer device also maintains the articular space of the implantation site, avoiding any shortening or atrophy of the surrounding tissues that could occur—in the absence of the spacer device itself—following the removal of the first prosthesis and awaiting the healing of the site of interest before the implantation of the new prosthesis.

This procedure is identified as a "two-stage implant" of the joint prostheses.

Modular spacer devices are also known, which may have different sizes or dimensions, in order to adapt as closely as possible to the anatomical dimensions of the patient.

These spacers are preformed and have predetermined sizes, and therefore the possibility of combining the various components in different sizes allows the surgeon to choose the most suitable spacer device, based on the specific surgical needs.

OBJECTS OF THE INVENTION

The present invention proposes the technical task of improving the prior art in the field of spacer devices for the joints of the human body.

Within the scope of this technical task, it is an object of the present invention to provide a spacer device for a joint of the human body, such as for example the knee joint, provided with at least one stem for connection to the bone of the human body surrounding the joint in question.

A further object of the present invention is to provide a spacer device for a joint of the human body that can be adapted to the patient's surgical needs.

A still further object of the present invention is to provide a spacer device for a joint of the human body which allows a stable articulation to the patient's bones surrounding the joint in question.

According to an aspect of the present invention, a spacer device is provided for a joint of the human body according to claim 1.

The dependent claims refer to preferred and advantageous embodiments of the invention.

BRIEF DESCRIPTION OF THE DRAWINGS

Further features and advantages of the present invention will become apparent from the detailed, non-exclusive description of an exemplary embodiment of a spacer device for a joint of the human body according to the present invention, given by way of non-limiting example in the accompanying drawings tables, in which:

FIG. 4A is a perspective view of a spacer device according to the present invention in an assembled version;

FIG. 4B is a partially sectional perspective view of the spacer device in FIG. 4A;

FIG. 5A is a perspective view of a spacer device according to the present invention in a version not completely assembled;

FIG. 5B is a partially sectional perspective view of the spacer device in FIG. 5A;

EMBODIMENTS OF THE INVENTION

Figure 1:
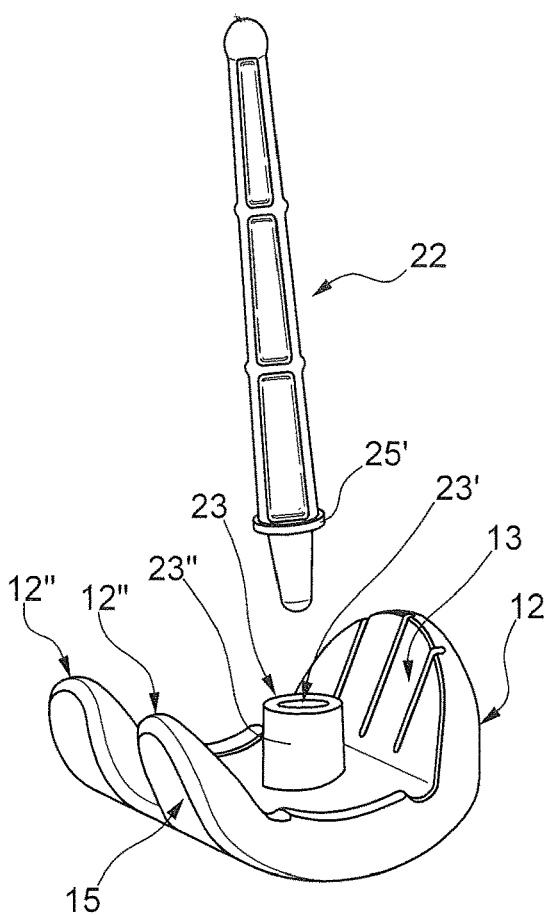
FIG. 1 is a perspective view of a component of a spacer device according to the present invention in a version not completely assembled.

With reference to the accompanying figures, a spacer device according to the present invention for a joint of the human body, for example for a knee joint, is globally indicated with reference numeral 10.

The spacer device 10 comprises a first component or femoral component 12 and a second component or tibial component 14.

The first component or femoral component 12 is adapted to be constrained, in use, to a patient's bone or femoral bone, at the knee joint, for example.

The second component or tibial component 14 is adapted to be constrained, in use, to a patient's bone or tibial bone, at the knee joint, for example.

Hereinafter, the femoral component 12 and the tibial component 14 will be referred to, but it will be understood that a first component 12 and a second component 14 for a joint of the human body, also different from a knee joint, may be included in a more generic manner.

The femoral component 12 is adapted to articulate, in use, on the tibial component 14. The spacer device 10 according to the present invention further comprises at least one stem 22, 24, for example a first stem 22 and a second stem 24.

According to a version of the invention, the first stem 22 is placed at the femoral component 12 and/or the second stem 24 at the tibial component 24, or vice versa.

The femoral component 12 has a substantially "C" configuration (considering a top plan view thereof) and/or a substantially U-shaped configuration (considering a side view thereof).

Figure 2:
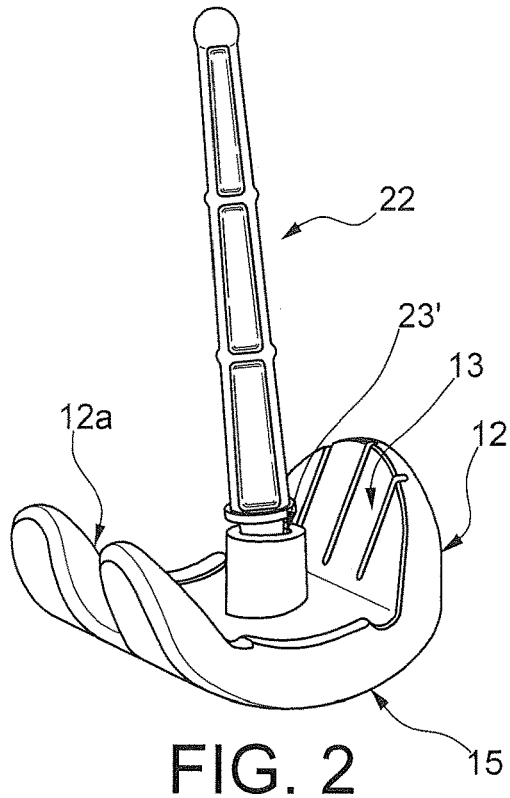
FIG. 2 is a perspective view of a component of a spacer device in FIG. 1 in an assembled version.
Figure 3:
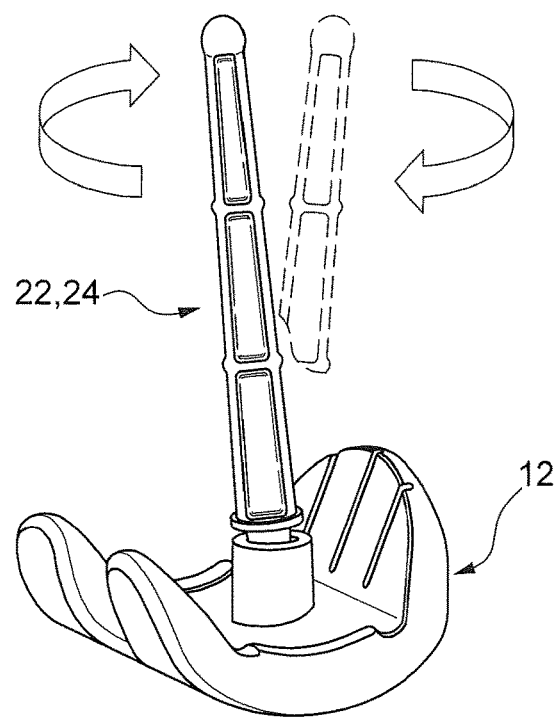
FIG. 3 is a perspective view of a component of a spacer device in FIGS. 1 and 2, showing the operation thereof.

Moreover, as visible for example in FIGS. 1 and 2, the femoral component 12 comprises a first surface 13, adapted in use to face and/or be constrained to the bone of a patient, for example the femoral bone at the knee joint, and a second surface 15, adapted in use to face the tibial component 14.

Likewise, as visible for example in FIGS. 5A and 5B, the tibial component 14 comprises a first surface 17, adapted in use to face and/or be constrained to the bone of a patient, for example the tibial bone at the knee joint, and a second surface 19, adapted in use to face the femoral component 12.

According to a version of the invention, for example shown in FIGS. 4A, 4B, 5A and 5B, an insert 16 can be interposed between the first surface 17 and the patient's bone.

Entering more in detail, the first surface 13 of the femoral component 12 has a concave, substantially "U" shape, considering a side view thereof.

By analogy, the second surface 15 of the femoral component has a shape substantially similar to that of the first surface 13 but opposite, that is to say convex. The second surface 15 also has a substantially "U" shape, considering a side view thereof.

At the first surface 13 of the femoral component 12 there is a housing seat 23 (or first housing seat 23) for the at least one stem 22, 24, in particular for example for the first stem 22.

According to a version of the invention, said housing seat 23 has a cavity 23'.

The housing seat 23 may comprise, according to an embodiment example, a housing wall 23". The housing wall 23" delimits the cavity 23'. Alternatively, the latter can be delimited directly into the body of the femoral component 12, without however affecting the second surface 15, adapted to precisely articulate with the tibial component 14.

In this case, the housing seat 23 could be obtained directly on the femoral component 12.

The housing seat 23 can be made in one piece with the femoral component 12, according to at least one version of the invention.

In the version in which the housing wall 23" is present, it departs from the first surface 13 away from the latter and/or extending towards the patient's bone.

The spacer device 10 according to the present invention, in addition to or as an alternative to the foregoing, may have, at the first surface 17 of the tibial component 14, a housing seat 27 (or second housing seat 27) for at least one stem 22, 24, in particular for example for the second stem 24.

According to a version of the invention, said housing seat 27 has a cavity 27'.

The housing seat 27 may comprise, according to an embodiment example, a housing wall 27". The housing wall 27" delimits the cavity 27'. Alternatively, the latter can be delimited directly into the body of the tibial component 14, without however affecting the second surface 19, adapted to precisely articulate with the femoral component 12.

In the version in which the housing wall 27" is present, it departs from the first surface 17 away from the latter and/or extending towards the patient's bone.

The features of the housing seat 23 and those of the housing seat 27 may be similar, at least in a version of the invention.

The femoral component 12 has a front portion 12', adapted in use to be positioned at the front of the knee joint of a patient, and two rear projections 12", adapted in use to be positioned at the back of the knee joint of a patient.

The two rear projection portions 12" correspond to the free ends of the "C" configuration of the plan configuration of the femoral component 12.

Between the two rear projections 12" there is a recess 12a. The recess 12a departs from the rear portion of the femoral component 12 up to approximately a central portion of the femoral component 12 itself.

The central portion of the femoral component 12 corresponds to a portion thereof comprised between the front portion 12', which extends upwards in use substantially vertically, and the two rear projection portions 12", also having a course slightly inclined upwards.

This central portion is substantially flat or has a slight curvature.

In the area of the central portion between the recess 12a and the front portion 12' is placed the housing seat 23.

In a version of the invention, in combination with or alternative to the one described above, the tibial component 14 has a substantially "C" configuration (considering a top plan view thereof) and/or a substantially constant thickness.

The first surface 17 of the femoral component 14 has a substantially flat or slightly curved pattern, adapted to articulate with the second surface 15 of the femoral component 12.

The second surface 19 of the tibial component 14 is also substantially flat.

Similar to what has been described above, in the tibial component 14 it is possible to identify a front portion 14' adapted in use to be positioned at the front of the knee joint of a patient, and two back extensions 14", adapted in use in be placed in the back portion of a patient's knee joint.

The two rear extensions 14" correspond to the free ends of the "C" configuration of the plan configuration of the tibial component 14.

Between the two rear extensions 14" there is a recess 14a. The recess 4a departs from the rear portion of the tibial component 14 up to approximately a central portion of the tibial component 14 itself.

At the second surface 19 and the central portion of the tibial component 14, the housing seat 27 (or further seat 27) is positioned.

If the insert 16 is present, it may have a pattern and shape and conformation substantially corresponding to those of the tibial component 14.

Moreover, it can have an opening 16', placed in use at the housing seat 27 and adapted to house, in turn, this housing seat 27.

Therefore, the conformation of the opening 16' has a shape and dimensions that allow insertion, inside the same, of the housing seat 27.

Figures 7A, 7B:
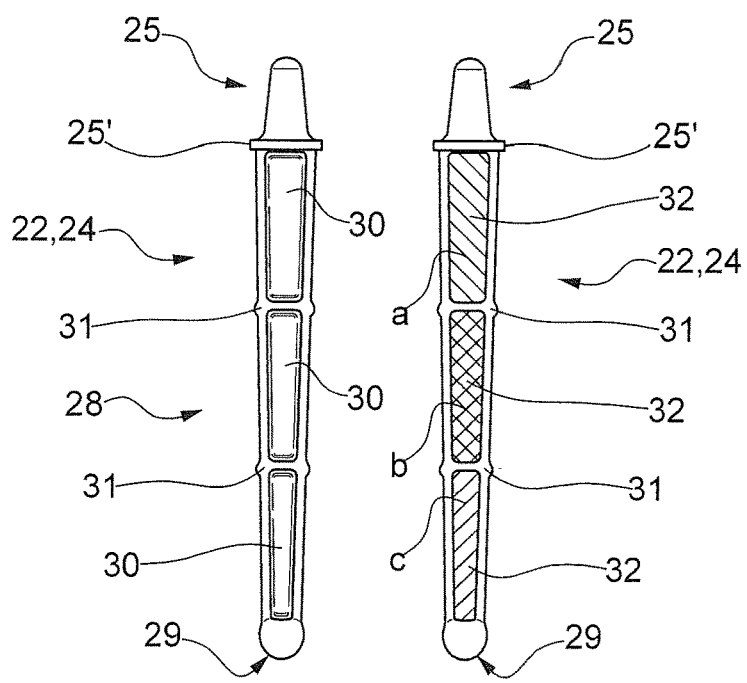
FIGS. 7A and 7B are front views of a stem of a spacer device according to the present invention respectively in a version comprising filling material and not comprising filling material.

Entering the detail of the shape of the at least one stem 22, 24, as visible for example in FIGS. 7A and 7B, said at least one stem has a rod-shaped configuration.

The at least one stem 22, 24 has an elongated body 28 and a proximal end 25, adapted in use to be housed inside the housing seat 23, 27, and in particular inside the cavity 23', 27'.

In at least one version of the invention, the proximal end 25 of the at least one stem has a substantially conical or pyramidal or truncated cone shape.

The proximal end 25, in at least one of its versions, has a rounded tip, corresponding to the vertex of the cone or pyramid or truncated cone and a base having a circular or polygonal section.

The base of the proximal end 25 is connected (possibly in one piece) to a base 25' of the elongated body 28 of the at least one stem.

The at least one stem 22, 24 further has a further end 29, or distal end 29, opposite the proximal end 25.

The cavity 23', 27', adapted to house the proximal end 25, has a shape adapted to allow the inclination and/or rotation of the proximal end 25, and therefore of the at least one stem 22, 23, around the insertion axis X of the proximal end 25 into the cavity 23', 27'. The possibility of adjusting the inclination occurs by tilting the stem 22, 24 at least both on the frontal plane and on the sagittal plane.

In a version of the invention, the wall 23", 27" is substantially parallel to the insertion axis X of the at least one stem 22, 24 inside the at least one seat 23, 27. In addition or as an alternative, the wall 23", 27" can be substantially perpendicular to the central portion of the femoral component 12 itself and/or of its first surface 13 and/or the first surface 17 of the tibial component 14.

In a further version, the wall 23", 27" is not perpendicular to these surfaces but rather inclined with respect to them.

Likewise, the inner lateral surface of the at least one cavity 23', 27' may be perpendicular or inclined with respect to such surfaces and the inner base wall of the at least one cavity 23', 27' may be perpendicular to the insertion axis X or inclined with respect to it. If such inner base wall is inclined, it can follow the course of the first surface 13, 17 of the femoral 12 and/or tibial 14 component, respectively.

The configuration of the cavity 23', 27' is, according to a version, substantially cylindrical, in order to house a conical proximal end 25 or another of the indicated shapes.

More generally, the shape of the cavity 23', 27' is conical or cylindrical or pyramidal or truncated cone or in any case of a shape adapted to loosely house and thus allowing the inclination or rotation of the at least one stem 22, 24 relative to the insertion axis X of the proximal end 25 into the housing seat 23, 27.

In these cases, the widest part of the cavity 23', 27' is the furthest from the first surface 13, 17 on which there is at least one housing seat 23, 27, so as to create a gap or opening for the insertion of the proximal end 25.

Therefore, between the at least one housing seat 23, 27 and the at least one stem 22, 24 there is a loose coupling, so as to allow the inclination and/or rotation of the at least one stem 22, 24 inside the housing seat 23, 27, with respect to the insertion axis of the at least one stem 22, 24 itself.

To achieve this, as stated, the housing seat 23, 27 could also have a shape similar or equal to that of the proximal end 25 but determining a space of greater size than the latter, just to allow the inclination of the stem 22, 24 with respect to the same.

More in detail, at least in a version of the invention, the depth of the cavity 23', 27' and/or of the housing seat 23, 27 is substantially corresponding and/or slightly greater than the length of the proximal end 25 of the at least a stem 22, 24.

Furthermore, the gap or opening of the at least one cavity 23', 27' is substantially greater than the diameter or cross-section of the proximal end 25 (so as to allow insertion thereof). In this way, there is free space between the inner walls of the cavity 23', 27' and the proximal end 25 which allow, precisely, the inclination and/or rotation of the at least one stem 22, 24.

However, in at least one version of the invention, the gap or opening of the at least one cavity 23', 27' may have slightly smaller dimensions than those of the base 25', so as to allow the latter to rest on the peripheral top edge of the wall 23", 27".

The peripheral upper edge of the wall 23", 27" is intended to be the upper edge further away from the first surface 13 and/or the first surface 17 respectively of the femoral component 12 and/or the tibial component 14.

Figure 6:
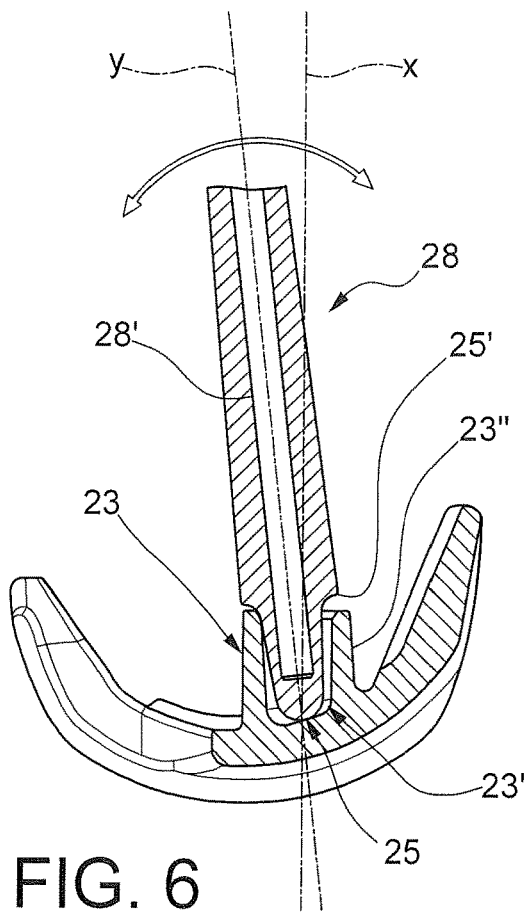
FIG. 6 is a view of an enlarged detail of a component of a spacer device according to the present invention.

The base 25' may be substantially flat or slightly inclined and/or tapered (as seen in FIG. 6) with respect to the proximal end 25.

The elongated body 28 extends between the proximal end 25 and the distal end 29, along a symmetry or longitudinal axis Y.

According to a version, the at least one housing seat 23, 27 may have a sleeve conformation.

It is understood that, if the surgical needs do not require the presence of a stem 22, 24, the spacer device 10 according to the present invention may be implanted equally, without limitations.

The elongated body 28 has a rod-like pattern which, at least in a version of the invention, has a tapered thinning pattern towards the distal end 29 with respect to the proximal end 25.

The at least one stem 22, 24 according to the present invention is a diaphyseal stem, i.e. insertable into the diaphysis of the patient's femoral and/or tibial bone. The presence of a stem 22, for the femoral component 12, and/or a stem 24, for the tibial component 14, or both or none of them varies according to the surgical needs and choice of the physician. This aspect also depends on the type of prosthesis that is removed before the implantation of the spacer device 10, since the prostheses can be equipped with one or more of these stems and therefore, to better treat any infection, it is advisable to insert a stem where the original prosthesis, then infected, included a corresponding stem.

The elongated body 28 has a section (transverse to its elongated shape) of substantially circular or polygonal shape.

If the section of the elongated body 28 is polygonal, there may be present therein, for example, a first longitudinal face and a second longitudinal face, substantially parallel to each other. In such a version, such faces may be positioned laterally and medially or frontally and posteriorly, with respect to the human body or bone in which the at least one stem 22, 24 must be inserted.

Alternatively, in the case in which the elongated body section 28 is circular, the outer wall of the at least one stem 22, 24 has a circular surface.

The elongated body 28 and/or at least one the first and second faces thereof, may comprise, at least in one version of the invention, at least one recess 30.

This at least one recess 30 has a substantially longitudinal and/or parallel path to the axis Y of the at least one stem 22, 24.

Moreover, this at least one recess 30 has a depth (i.e. is within the elongated body 28) in a much smaller ratio with respect to its extension in plan and/or its longitudinal length and/or parallel to the axis Y of the at least one stem 22, 24.

Again, this at least one recess has a substantially rectangular or trapezoidal shape with rounded corners, wherein the short side is at the proximal 25 and/or distal 29 end while the long side is parallel to the axis Y of the at least one stem 22, 24.

Thus, the length of the at least one recess 30 is greater than its width and much greater than its depth.

In the embodiment illustrated by way of example in FIGS. 7A and 7B, the stem 22, 24 has three recesses per side or face, placed one after the other, aligned along the axis Y of the at least one stem.

These recesses are interspersed with intermediate ribs 31, each extending towards the outside of the stem 22, 24, arriving flush or continuing beyond the outer surface of the elongated body 28.

Such ribs 31 can be parallel and similar to the base 25'.

In at least one version, for example, when the cross section of the elongated body 28 is substantially circular, the at least one recess 30 may be placed radially with respect to the axis Y of the stem 22, 24. Alternatively, the at least one recess 30 may have an annular band pattern extending, recessing towards the inside of the stem 22, 24, as a sort of recessing band with respect to the stem 22, 24 itself, with center in the axis Y.

Also in this case, the depth of the at least one recess 30 is smaller than its length and circular extension.

Of course, with respect to the number of recesses 30 illustrated, it is possible to have one or more recesses and consequently one or more ribs 31, depending on the length of the stem 22, 24 and according to the needs.

The stem 22, 24 can, in fact, have a length between 5 cm and 30 cm depending on the anatomical shape of the patient.

An advantage of the present invention, provided that the stems 22, 24 can be inserted into suitable housing seats 23, 27, is that the stems themselves are interchangeable, and the surgeon can select the stem that best suits his needs, selecting the length thereof, the dimensions, and the number of recesses 30 present therein, provided that these recesses are present.

Inside the at least one recess 30, at least one filling material 32 may be present in at least one version of the invention.

In one version of the invention, the filling material 32 comprises an acrylic bone cement, such as, for example, polymethyl methacrylate or PMMA, or another suitable material.

In a further version of the invention, the filling material 32 can comprise any solid, fluid and/or viscous filling material adapted to convey at least one pharmaceutical or medical substance and to release such at least one pharmaceutical or medical substance slowly over time, in order to obtain an extended and long-lasting pharmacological effect.

The filling material 32 comprises at least one pharmaceutical or medical substance, such as at least one antibiotic.

In a version of the invention, in each recess 30, a filling material 32 containing a different pharmaceutical or medical substance, e.g. a substance a and/or b and/or c can be positioned (or applied or inserted) (as illustrated in FIG. 7B).

The shape of the recess 30 allows it to be rapidly filled by the surgeon, prior to implantation of the stem 22, 24 and the spacer device 10, according to the specific needs of the patient.

In this embodiment, the surgeon can fill such at least one recess 30 in an ordered manner, that is to say, not beyond the peripheral edge of the recess 30 itself and/or of the rib 31. Such edges and/or ribs are easily visually visible to the surgeon.

In this way, the filling material 32 will be positioned flush with respect to the outer surface of the elongated body 28 of the at least one stem 22, 24.

In a further version, in combination or alternative with respect to what has been described above, it is possible to position, in each recess 30, a different filling material 32, possibly admixed with the same pharmaceutical or medical substance or with different pharmaceutical or medical substances a, b, c, at least one in each recess 30.

As regards the assembly method of the at least one stem 22, 24, after having provided a femoral component 12 and/or a tibial component 14, each provided with at least one respective housing seat 23, 27, the cavity 23', 27' of the at least one housing seat 23, 27 is filled with fresh and/or fluid bone cement (such as an acrylic or polymethyl methacrylate bone cement).

In this cavity 23', 27', the proximal end 25 of at least one stem 22, 24 is housed or inserted.

This end 25 is inserted or housed along a direction corresponding to the insertion axis X thereof.

The proximal end 25, therefore, is inserted into the bone cement.

Then, in use, the spacer device 10 of the articular seat of interest is implanted, and the at least one stem 22, 24 is inserted into the diaphyseal canal of the femoral and/or tibial bone, respectively.

Due to the fact that the stem 22, 24 is adapted to be inclined and/or to rotate with respect to the insertion axis in the housing seat 23, 27, it will be possible to orient the stem itself along the specific direction of the diaphysis of interest, thus allowing to follow the inclination of the medullary canal without problems. The mobility of the at least one stem 22, 24 is allowed due to the fact that in this time, the bone cement present in the housing seat 23, 27 is still in a fluid state.

After having correctly oriented the at least one stem 22, 24, and having completed the implantation of the spacer device 10, after a few minutes, the bone cement will become solid, polymerizing, locking in position the at least one stem 22, 24.

In a preferred but non-limiting embodiment of the invention, the spacer device 10 comprises both a stem 22, for the femoral component 12, and a stem 24, for the tibial component 14.

The at least one stem 22, 24 may comprise an inner core 28', possibly made of metal material, to give greater stiffness and solidity to the stem itself.

This core 28' may be internal to the elongated body 28 and have a substantially rod-like conformation, possibly with a cylindrical cross-section.

Finally, it is possible that at least one of the femoral component 12, tibial component 14, insert 16 and at least one stem 22, 24 are provided in various sizes (for example a small size, a medium size and/or a large size) to better adapt to the patient's anatomical needs. These measures or sizes can be combined with all the sizes of the other components, in order to provide better variability and choice for the surgeon.

To achieve this, the inclination of the surfaces in contact between the femoral component 12, the tibial component 14 and the insert 16, when present, is substantially unchanged as the size changes, so as to allow it to be assembled anyway.

Similarly, the position and/or dimensions of the at least one seat 23, 27, of the opening 16' (when the insert 16 is present) and the size of the proximal end 25 will be substantially unchanged as the size of the components and/or of the stem changes, so as to allow it to be assembled anyway.

The present invention therefore also includes a kit for the construction and/or composition of a spacer device 10 according to the present invention.

Each element or component of the spacer device 10 is made of a biocompatible material, such as acrylic bone cement, optionally based on or comprising polymethyl methacrylate (PMMA).

According to a version of the invention, the biocompatible material can comprise a plastic material, possibly thermoformable, such as polyvinylchloride (PVC), polystyrene (PS), polyethylene (PE), very high molecular weight polyethylene (UHMWPE), high or low density polyethylene, etc., or a non-polymeric material, a ceramic material, a metal, a metal alloy, an organo-metallic compound, etc. and/or a combination thereof.

The biocompatible material can be porous and/or provided with interconnected pores and/or canaliculi and be therefore adapted to absorb and subsequently release a pharmaceutical or medical substance supplied in the form of an aqueous solution or a fluid form.

Likewise, the filling material 32 can be porous and/or provided with interconnected pores and/or canaliculi and therefore be adapted to absorb and subsequently release the pharmaceutical or medical substance a, b, c, the latter supplied in the form of aqueous solution or fluid form.

The filling material 32 can be solid or a solidifiable fluid.

In one version of the invention, the at least one stem 22, 24 may already be provided with the filling material 32 inside the at least one recess 30.

It has thus been seen that the present invention can adapt to the patient's specific surgical and anatomical needs, providing a spacer device 10 provided with at least one stem 22, 24, adapted to be oriented (inclining and/or rotating it) according to the specific direction of the diaphyseal channel in which it must be inserted in use.

The spacer device 10 according to the present invention is susceptible of numerous modifications and variations within the scope of protection of the following claims.

The invention claimed is:

1. A temporary spacer device, for an articulation of a human body, comprising
    a first component or femoral component, adapted to be constrained to a first bone or to a femoral bone of a patient, at a joint of the human body;
    a second component or tibial component, adapted to be constrained to a second bone or tibial bone of the patient, at the joint of the human body; and
    at least one stem having a proximal end, a distal end, and an elongated body therebetween, said elongated body defining a longitudinal axis,
    wherein one or both of said first component or femoral component and said second component or tibial component comprise at least one housing seat for said proximal end of said at least one stem, so as to allow a change in inclination with respect to said housing seat and/or a rotation of said at least one stem with respect to an insertion axis of said proximal end in said at least one housing seat,
    wherein said elongated body comprises at least one recess containing a filling material, and
    wherein said filling material comprises an acrylic bone cement, or a solid, fluid and/or viscous material adapted to convey and release at least one pharmaceutical or medical substance, and at least one pharmaceutical or medical substance.

2. The temporary spacer device according to claim 1, wherein said at least one stem comprises one or both of a first stem, placed at said first component or femoral component and/or a second stem, placed at said second component or tibial component, or vice versa.

3. The temporary spacer device according to claim 1, wherein said first component or femoral component has one or more of a "C"-shaped configuration in plan view from above, a "U"-shaped lateral configuration, or a first surface, configured to face or to be constrained to the first bone or to the femoral bone, and a second surface, configured to face said second component or tibial component, and wherein said first surface has a concave shape, configured as a "U", and said second surface has a convex shape, configured as a "U".

4. The temporary spacer device according to claim 3, wherein said second component or tibial component has one or more of a "C"-shaped configuration in plan view from above, or comprises a first surface, configured to face and/or be constrained to the second bone or the tibial bone, and a second surface, configured to face said first component or femoral component, or comprises an insert, provided with an opening for housing a second housing seat of said at least one housing seat and/or said stem, wherein said insert is configured to be interposed between said first surface and the second bone or the tibial bone of the patient.

5. The temporary spacer device according to claim 4, wherein said at least one housing seat comprises a first housing seat, placed at said first surface of said first component or femoral component or a second housing seat, located at said first surface of said second component or tibial component, wherein said at least one housing seat comprises at least one cavity, for housing said proximal end of said at least one stem.

6. The temporary spacer device according to claim 5, wherein said at least one housing seat comprises a first housing wall, wherein said first housing wall delimits said at least one cavity and departs from said first surface of said first component or femoral component moving away from the first component or femoral component and/or extending towards the first bone or femoral bone of the patient, and/or wherein said housing seat comprises a second housing wall, wherein said second housing wall delimits said at least one cavity and departs from said first surface of said second component or tibial component moving away from the second component or tibial component and/or extending towards the second bone or tibial bone of the patient.

7. The temporary spacer device according to claim 6, wherein said proximal end has a conical, pyramidal, or frusto-pyramidal conformation.

8. The temporary spacer device according to claim 6, wherein said at least one cavity has a cylindrical, conical, pyramidal, frusto-conical, or frusto-pyramidal conformation, or a configuration to house in the slack or loose manner said proximal end and wherein said at least one cavity has a gap or opening for inserting said proximal end.

9. The temporary spacer device according to claim 8, wherein said at least one cavity has a depth corresponding and/or greater than a length of said proximal end of said at least one stem, or wherein said gap or opening has a size greater than the diameter of the cross-section of said proximal end but smaller than a size of a base of the elongated body of the at least one stem, wherein said base is connected to said proximal end.

10. The temporary spacer device according to claim 9, wherein said first or said second housing wall has a peripheral upper edge supporting said base of said at least one stem.

11. The temporary spacer device according to claim 10, wherein said elongated body presents a tapered thinning arrangement towards the distal end and/or a section crossing the longitudinal axis having a circular or polygonal shaped, and wherein said elongated body comprises a circular outer wall or a first longitudinal face and a second longitudinal face parallel to each other.

12. The temporary spacer device according to claim 11, wherein said elongated body and/or the circular outer wall of the elongated body and/or at least one of the first and second faces of the elongated body comprises the at least one recess, configured to contain the filling material, or wherein said elongated body and/or the circular outer wall and/or at least one of the first and second faces of the elongated body comprises the at least one recess and the filling material housed in said at least one recess.

13. The temporary spacer device according to claim 12, wherein said at least one recess has a longitudinal and/or parallel path to the longitudinal axis of the at least one stem and a depth of smaller size than an extension in plan of said at least one recess and/or a length of said at least one recess.

14. The temporary spacer device according to claim 12, wherein said at least one recess has a rectangular or trapezoidal shape with rounded corners, wherein a short side of the rectangular or trapezoidal shape is located at said proximal or distal end and a long side of the rectangular or trapezoidal shape is parallel to the longitudinal axis of said at least one stem or has an annular band conformation.

15. The temporary spacer device according to claim 12, wherein said at least one recess is alternated with respect to a subsequent at least one recess from at least one intermediate rib, and wherein said at least one rib is parallel to the base.

16. The temporary spacer device according to claim 6, wherein said first or said second housing wall is parallel to the insertion axis, or perpendicular to the first surface of said first component or femoral component and/or the first surface of said second component or tibial component, or is inclined with respect to the insertion axis or the first surface of said first component or femoral component or the first surface of said second component or tibial component.

17. The temporary spacer device according to claim 1, wherein said at least one stem comprises an inner core shaped as a rod.

18. The temporary spacer device according to claim 1, wherein said temporary spacer device or said at least one stem are preformed and made of a biologically compatible material, and wherein said biologically compatible material is porous or provided with interconnected pores and canalicoli.

19. A kit for realization of a spacer device, comprising:
the temporary spacer device according to claim 1, wherein said first component or femoral component, said second component or tibial component, and said at least one stem are each provided in different sizes; and
a filling material adapted to be received in one or more recesses defined on said at least one stem.

20. A temporary spacer device, for an articulation of a human body, comprising:
a first component or femoral component, adapted to be constrained to a first bone or to a femoral bone of a patient, at a joint of the human body;
a second component or tibial component, adapted to be constrained to a second bone or tibial bone of the patient, at the joint of the human body; and
at least one stem having a proximal end, a distal end, and an elongated body therebetween, said elongated body defining a longitudinal axis,
wherein one or both of said first component or femoral component and said second component or tibial component comprise at least one housing seat for said proximal end of said at least one stem, dimensioned to house the proximal end of the at least one stem in a slack or loose manner by having a diameter larger than a diameter of a cross-section of said proximal end so as to allow a change in inclination with respect to said housing seat and a rotation of said at least one stem with respect to an insertion axis of said proximal end in said at least one housing seat, and
wherein said elongated body comprises at least one recess configured to contain a filling material.

* * * * *